(12) United States Patent
Xu et al.

(10) Patent No.: US 9,310,347 B2
(45) Date of Patent: Apr. 12, 2016

(54) METHODS AND SYSTEMS FOR ANALYZING COMBUSTION SYSTEM OPERATION

(75) Inventors: Guang Xu, Santa Ana, CA (US); David Moyeda, Santa Ana, CA (US); Neil Widmer, Santa Ana, CA (US); Wei Zhou, Santa Ana, CA (US)

(73) Assignee: General Electric Company, Schenectady, NY (US)

( * ) Notice: Subject to any disclaimer, the term of this patent is extended or adjusted under 35 U.S.C. 154(b) by 1251 days.

(21) Appl. No.: 12/947,052

(22) Filed: Nov. 16, 2010

(65) Prior Publication Data

US 2012/0122040 A1    May 17, 2012

(51) Int. Cl.
| | |
|---|---|
| F23N 5/24 | (2006.01) |
| G01N 7/00 | (2006.01) |
| G01N 31/00 | (2006.01) |
| G01N 33/00 | (2006.01) |
| F23N 5/00 | (2006.01) |

(52) U.S. Cl.
CPC .............. *G01N 33/004* (2013.01); *F23N 5/003* (2013.01); *F23N 5/006* (2013.01); *G01N 33/0075* (2013.01)

(58) Field of Classification Search
CPC .. G01N 33/004; G01N 33/0075; F23N 5/003; F23N 5/006
USPC .............................. 431/2, 76; 73/23.31; 702/24
See application file for complete search history.

(56) References Cited

U.S. PATENT DOCUMENTS

| | | | |
|---|---|---|---|
| 5,091,844 A * | 2/1992 | Waltz ............................. | 700/33 |
| 6,289,299 B1 | 9/2001 | Daniel, Jr. et al. | |
| 6,474,271 B1 | 11/2002 | Widmer et al. | |
| 6,904,815 B2 | 6/2005 | Widmer | |
| 7,010,461 B2 * | 3/2006 | Draxton et al. ............... | 702/182 |
| 7,389,151 B2 | 6/2008 | Badami et al. | |
| 7,464,002 B2 | 12/2008 | Hayashi | |
| 7,469,647 B2 | 12/2008 | Widmer et al. | |
| 7,475,646 B2 | 1/2009 | Widmer et al. | |
| 7,581,945 B2 | 9/2009 | Widmer et al. | |
| 2004/0135821 A1 | 7/2004 | Mazzeo | |
| 2004/0191914 A1 | 9/2004 | Widmer et al. | |
| 2004/0255831 A1 * | 12/2004 | Rabovitser et al. ........... | 110/345 |

(Continued)

FOREIGN PATENT DOCUMENTS

CN        1795377 A        6/2006

OTHER PUBLICATIONS

Michel, J.B. et al: "State of the Art on Emerging Combustion Control Sensors", Proceedings of the Sixth International Conference on Technologies and Combustion for a Clean Environment, Jul. 9, 2001.

(Continued)

*Primary Examiner* — William Grant Corboy
(74) *Attorney, Agent, or Firm* — Sutherland Asbill & Brennan LLP

(57) ABSTRACT

Systems and methods for analyzing combustion system operation are provided. According to one embodiment, a method can include receiving multiple CO measurements from respective CO sensors distributed within a combustion system; receiving multiple $O_2$ measurements from respective $O_2$ sensors distributed within the combustion system; and determining at least one operating condition of the combustion system based at least in part on CO indicated by the CO measurements relative to $O_2$ indicated by the $O_2$ measurements.

21 Claims, 7 Drawing Sheets

(56) References Cited

U.S. PATENT DOCUMENTS

| | | |
|---|---|---|
| 2005/0063873 A1 | 3/2005 | Morris et al. |
| 2006/0155486 A1 | 7/2006 | Walsh et al. |
| 2007/0184556 A1 | 8/2007 | Wang |

OTHER PUBLICATIONS

Fogarty, T.C.: "Rule-based optimization of combustion in multiple-burner furnaces and boiler plants", Engineering Applications of Artificial Intelligence UK, vol. 1, No. 3, Sep. 1988, pp. 203-209.

Docquier, N. et al: "Combustion control and sensors: a review", Progress in Energy and Combustion Science, Elsevier Science Publishers, Amsterdam, NL, vol. 28, No. 2, Jan. 1, 2002, pp. 107-150.

EP Search Report and Opinion dated May 10, 2012 from corresponding EP Application No. 111888187.6.

Unofficial English translation of Office Action issued in connection with corresponding CN Application No. 201110391737.7 on Mar. 23, 2015.

* cited by examiner

METHODS AND SYSTEMS FOR ANALYZING COMBUSTION SYSTEM OPERATION

TECHNICAL FIELD

The invention relates generally to combustion systems, and more particularly relates to methods and systems for analyzing combustion system operation.

BACKGROUND OF THE INVENTION

In numerous industrial environments, a hydrocarbon fuel is burned in stationary combustors (e.g., boilers or furnaces) to produce heat to raise the temperature of a fluid, such as water. For example, water is heated to generate steam, which is then used to drive turbine generators that output electrical power. Such industrial combustors typically employ an array of many individual burner elements to combust the fuel. In addition, various combustion control techniques, such as overfire air, staging air, reburning systems, and selective non-catalytic reduction systems, can be employed to enhance combustion conditions and reduce oxides of nitrogen ("$NO_x$") emission.

For a combustor to operate efficiently and to produce an acceptably complete combustion that generates by-products falling within the limits imposed by environmental regulations and design constraints, all individual burners in the combustor should operate cleanly and efficiently, and all combustion modification systems should be properly balanced and adjusted. Emissions of $NO_x$, carbon monoxide ("CO"), mercury ("Hg"), and/or other by-products (e.g., unburned carbon or loss-on-ignition ("LOI") data) generally are monitored to provide compliance with environmental regulations and acceptable system operation. The monitoring heretofore has been done, by necessity, on the aggregate emissions from the combustor, such as on the entire burner array, taken as a whole, without providing an analysis on each individual burner and/or varied conditions within the burner.

Some emissions, such as the concentration of unburned carbon in fly ash and Hg can be difficult to monitor online and continuously. In many cases, these emissions are conventionally measured on a periodic or occasional basis by extracting a sample of ash and sending the sample to a laboratory for analysis. When a particular combustion by-product is found to be produced at unacceptably high concentrations, the combustor is adjusted to restore desired operating conditions. Measurement of the aggregate emissions, or measurement of emissions on a periodic or occasional basis, however, does not provide an indication of what combustor parameters should be changed and/or which combustor zone should be adjusted.

The air-to-fuel ratios between each burner in a combustor of a boiler can vary considerably because the burner air and pulverized coal distributions can vary significantly from burner to burner. The absence of effective methods to adequately monitor and control the coal and air flows can contribute to a boiler not operating under its optimal combustion conditions. The variance in burner coal and air flow rates can lead to a wide variance in individual burner operating conditions, some operating on the fuel-rich side and some on the fuel-lean side of the average boiler air-to-fuel ratio. The burners operating on the fuel-rich side produce significant unburned combustion by-products (e.g., CO and LOI) that may not be completely oxidized downstream by mixing with excess air from fuel-lean burners. The degree to which a fuel-rich burner's unburned by-products are oxidized depends on the proximity of the fuel-lean burners, the degree of mixing, and the mixed burner stream temperature. The final unburned by-product levels restrict the boiler from operating at lower excess air levels, which has the effect of driving fuel-rich burners richer and producing more unburned by-products, as well as reducing the availability of excess air from fuel-lean burners to burn-out by-products of the fuel-rich burners. One result of these out of balance burner conditions is that boilers may be operated at higher excess air levels. The levels of excess air are dictated by the amount of imbalance in the burner's air-to-fuel ratios. As a result of the operation under high excess air, there can be an increase in $NO_x$ emissions and a reduction in the boiler's efficiency, which increases operational costs for fuel and $NO_x$ credits and also reduces output due to emissions caps.

In some plants, boilers are operated with high excess air in order to increase combustion gas mass flow and subsequent heat transfer in the convective pass to achieve desired steam temperatures. In these applications, burner imbalance can have an impact on gas temperature uniformity. For fossil fuel fired boilers, peak combustion temperatures are reached at slightly fuel-rich operation. These peak temperatures caused by fuel-rich burners can lead to increased metal fatigue, slagging (melted ash) deposits on convective passes, corrosive gases, and high ash loadings in local convective pass regions. To remove ash and slagging, additional sootblowing is required. Sootblowing, high temperature gases, and corrosive gases can lead to the deterioration of watertube and waterwall metals, which can result in frequent forced outages due to tube or other component failures and, thus, lost power generation capability. Currently, to avoid potentially catastrophic failure due to high temperature metal fatigue in convective passes, the boiler may be "derated." This means the boiler is operated below the rated capacity, which reduces the total heat input and reduces the gas temperature exiting the furnace prior to the convective passes.

Thus, there exists a need for improved methods and systems for analyzing boiler operation.

BRIEF DESCRIPTION OF THE INVENTION

Embodiments of the invention can address some or all of the needs described above. According to one embodiment, a method for analyzing combustion system operation is provided. The method can include: receiving multiple CO measurements from respective CO sensors distributed within a combustion system; receiving multiple $O_2$ measurements from respective $O_2$ sensors distributed within the combustion system; and determining at least one operating condition of the combustion system based at least in part on CO indicated by the CO measurements relative to $O_2$ indicated by the $O_2$ measurements.

According to another embodiment, a system for analyzing combustion system operation is provided. The system can include at least one controller in communication with multiple CO sensors associated with a combustion system and multiple $O_2$ sensors associated with the combustion system. The controller may be operable to: receive multiple CO measurements from respective CO sensors; receive multiple $O_2$ measurements from respective $O_2$ sensors distributed; and determine at least one operating condition of the combustion system based at least in part on CO indicated by the CO measurements relative to $O_2$ indicated by the $O_2$ measurements.

According to yet another embodiment, a method for analyzing combustion system operation is provided. The method can include: receiving a first group of CO measurements from respective CO sensors distributed within a combustion system at a first point in time and receiving a second group of CO measurements from the respective CO sensors at a second point in time; receiving a first group of $O_2$ measurements from respective $O_2$ sensors distributed within the combustion system at the first point in time and receiving a second group of $O_2$ measurements from the respective $O_2$ sensors at the second point in time. The method may further include: determining the combustion system is in steady state operation based on a temporal standard deviation calculation based on at least one of (a) the first and the second group of CO measurements or (b) the first and the second group of $O_2$ measurements; and adjusting combustion system operation based at least in part on levels of CO indicated by the second group of CO measurements relative to levels of $O_2$ indicated by the group plurality of $O_2$ measurements.

Other embodiments and aspects of the invention will become apparent from the following description taken in conjunction with the following drawings.

DETAILED DESCRIPTION OF THE INVENTION

Figure 1:
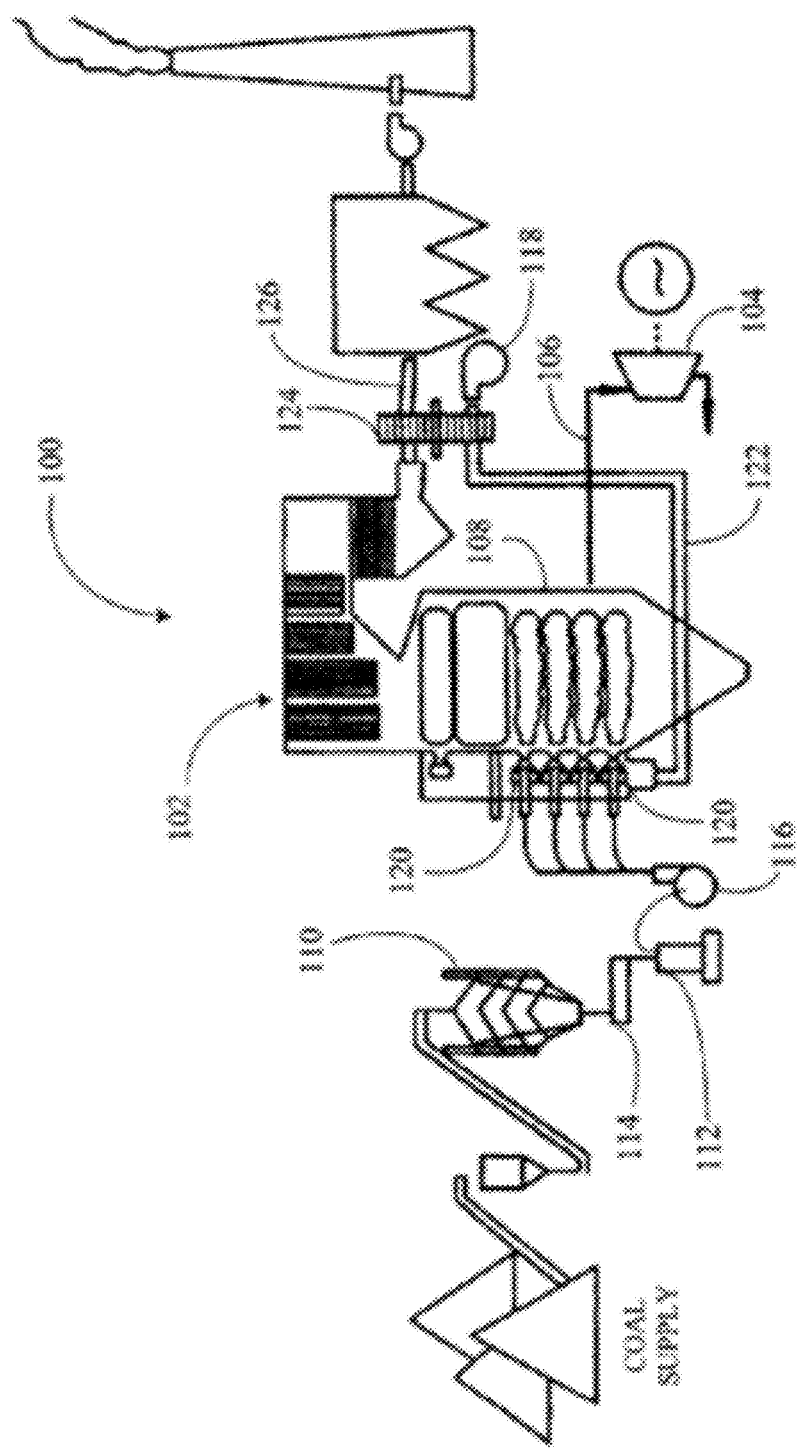
FIG. 1 is a schematic representation of a power generating system including a boiler, according to an example embodiment.

Example embodiments of the invention now will be described more fully hereinafter with reference to the accompanying drawings, in which some, but not all embodiments are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

According to an example embodiment of the invention, combustion system operation can be analyzed by comparing multiple CO measurements with multiple $O_2$ measurements taken from multiple CO sensors and $O_2$ sensors distributed throughout portions of the combustion system, such as within flue gas ducting. Example combustion systems can include, but are not limited to, boilers, furnaces, duct burning systems, kiln systems, and the like, which are referred to generally as combustion systems throughout. Although specific examples refer to boilers, the systems and methods described herein may be applied to any other combustion system as desired. One or more operating conditions of the combustion system or boiler can, thus, be determined based at least in part on the levels of CO indicated by the CO measurements relative to the levels $O_2$ indicated by the $O_2$ measurements. According to one embodiment, the relative comparison of CO versus $O_2$ can be analyzed by averaging the multiple CO measurements and the multiple $O_2$ measurements taken at different locations within the boiler, and comparing the CO average relative to the $O_2$ average to predefined thresholds. Moreover, a graphical or spatial comparison can be made if plotting the CO average relative to the $O_2$ average. Any number of plotting or graphing techniques may be employed to facilitate comparing CO and $O_2$ levels. In one embodiment, a quadrant graph composed of four individual quadrants defined by $O_2$ level along one axis and CO level along the other axis may be used. Boiler operating conditions can, thus, be inferred, depending upon the quadrant in which the measurement(s) are plotted, indicating the relative levels of CO and $O_2$. As one example, high levels of CO but low levels of $O_2$ may indicate an operating condition in which not enough fuel is burning, calling for raising the $O_2$ level, or low levels of both CO and $O_2$ may indicate desired operating conditions and not call for any boiler adjustments to be made.

According to various embodiments, in addition to plotting relative levels of CO and $O_2$, further mathematical analysis can be performed on the multiple measurements of the CO and $O_2$ levels. For example, in one embodiment, a spatial standard deviation of each of the CO levels and $O_2$ levels can be calculated, which can be utilized to indicate whether the CO and/or $O_2$ levels have significant variance at different locations within or are relatively consistent. Significant deviation of a given CO or $O_2$ level may indicate a need to balance the levels of CO or $O_2$. In one embodiment, these standard deviation calculations can be utilized in conjunction with the graphical plotting, to provide additional insight into the boiler operating condition and potential optimization or control actions to be taken, such as to increase or decrease $O_2$ levels, increase or decrease CO levels, increase or decrease fuel delivery, improve the fuel burning efficiency, etc.

Any of the above-described CO and $O_2$ level measurements and resulting calculations can be performed on data that is captured over time, also referred to as temporal measurements. Capturing data over time allows performing rolling or moving calculations to determine boiler operating conditions at the instant point in time based at least in part on a relative history. Additionally, any of the above-described CO and $O_2$ level measurements and resulting calculations can be performed on data from multiple sensors within the boiler for comparing CO and $O_2$ levels spatially within the boiler (at an instant point in time), which is referred to as spatial measurements.

Temporal measurements further allow determining whether the boiler is in steady state operation. In some circumstances, it may not be desirable to attempt to tune or optimize boiler operation if the boiler is not operating in a steady state. Thus, comparing data over time (e.g., a rolling standard deviation of temporal measurements) may first allow determining whether the operation of the boiler is still in flux or is operating at a relative steady state.

Example embodiments are now described with reference to FIGS. 1-9.

Referring to the drawings, FIG. 1 is a schematic view of an example power generating system 100 with a combustion system that includes a boiler 102 coupled to a steam turbine generator 104, according to one embodiment. Steam is produced in the boiler 102 and flows through a steam pipe 106 to the generator 104. The boiler 102 burns fossil fuel, for example, coal, in a boiler furnace 108, which produces heat to convert water into steam used to drive the generator 104. Of course, in other embodiments, the fossil fuel burned in the boiler 102 can be any number of other usable fossil fuels, such as, but not limited to, oil or natural gas, or biomass-type fuels.

Crushed coal can be stored in a silo 110 and is further ground or pulverized into fine particulates by a pulverizer or mill 112. A coal feeder 114 adjusts the flow of coal from the coal silo 110 into the mill 112. An air source, for example a fan 116, is used to convey the coal particles to the boiler furnace 108 where the coal is burned by multiple burners 120. The air used to convey the coal particles from the mill 112 to the burners 120 is referred to as primary air. A second fan 118 supplies secondary air to the burners 120 through an air conduit 122 and a windbox. The secondary air is heated by passing through a regenerative heat exchanger 124 located in a boiler exhaust line 126. It is appreciated that the power generating system 100 described is provided for illustrative purposes and is not intended to be limiting. The methods and systems described herein may be provided with any number of power generating system configurations, and as stated above, are not limited in their application to boilers.

Figure 2:
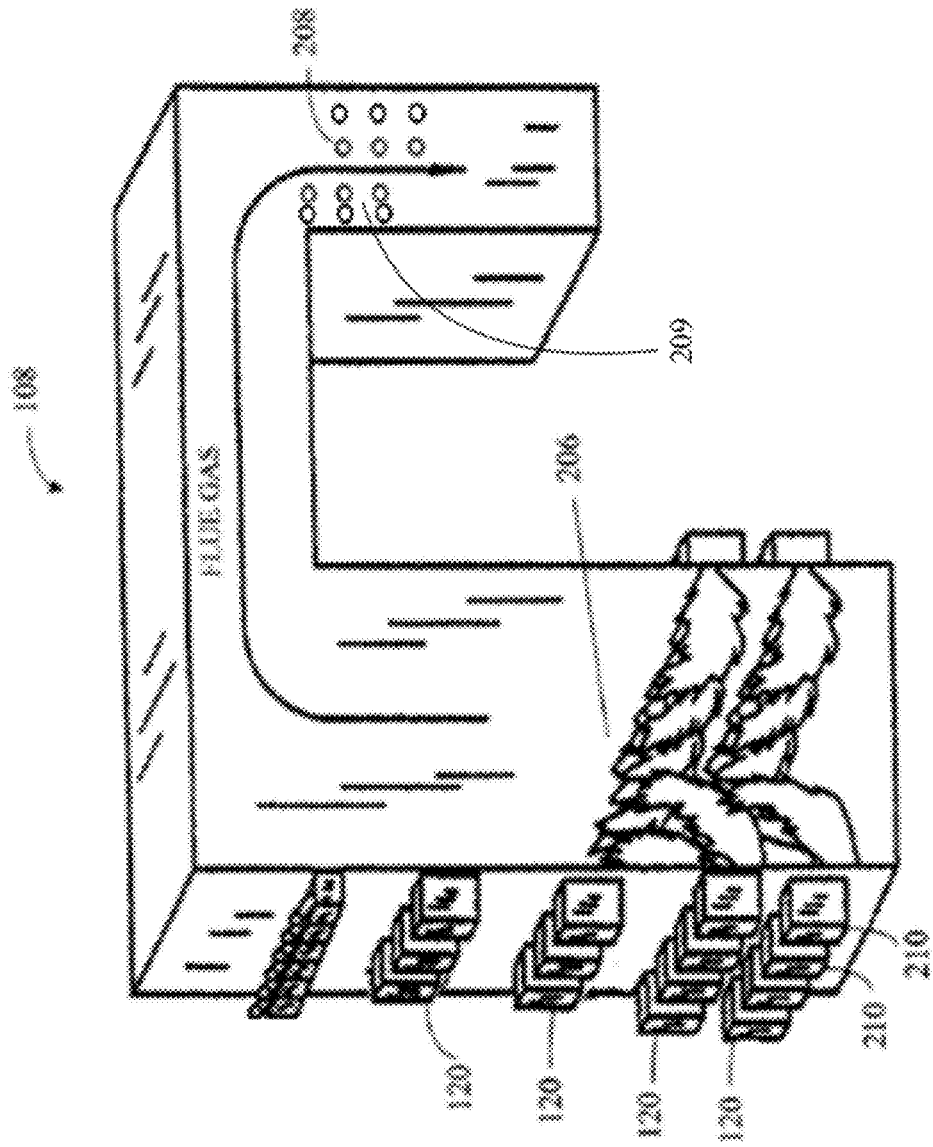
FIG. 2 is a schematic representation of a boiler, according to an example embodiment.

FIG. 2 is a schematic diagram of an example boiler, according to one embodiment. The boiler furnace 108 may include a grid of one or more CO sensors 208 which are located in an exit portion of the boiler furnace 108. An additional grid (also referred to herein as an "array") of one or more $O_2$ sensors 209 are also located in an exit portion of the boiler furnace 108. According to one embodiment, the location of these various sensors, such as the grid CO sensors 208 and the grid $O_2$ sensors 209 correspond to the burners 120, which are also in a grid arrangement. In other words, a CO sensor 208 and an $O_2$ sensor 209 can be located in alignment with each column 210 of the burners 120. According to one embodiment, one or more CO sensors 208 and one or more $O_2$ sensors 209 are grouped into one or more sensor groups, such that each sensor group represents an approximate location within the boiler, and measurements can be associated with the sensor groups.

Additional sensors, such as additional CO sensors 208 and/or additional $O_2$ sensors 209, may be located at an exhaust or smokestack. It is further appreciated that, according to various other embodiments, the CO sensors 208 and the $O_2$ sensors 209 may be located together at one or more different and/or additional locations within the boiler furnace 108, such as, but not limited to, near the superheat zone or in the reheat zone or at the exit plane (output) of the boiler furnace 108 so that each location in the grid will have the sensors (e.g., CO and $O_2$). In other embodiments of the invention, other types of sensors can be provided to monitor the combustion process occurring in boiler furnace 108, such as, but not limited to, $CO_2$ sensors, $NO_x$ sensors, and/or optical radiation sensors including variable components of the radiation sensors. For example, one or more loss of ignition ("LOI") sensors and one or more temperature sensors (not numbered) may be included in a grid formation located upstream from a flame envelope 206 formed by burning coal at the burners 120.

Figure 3:
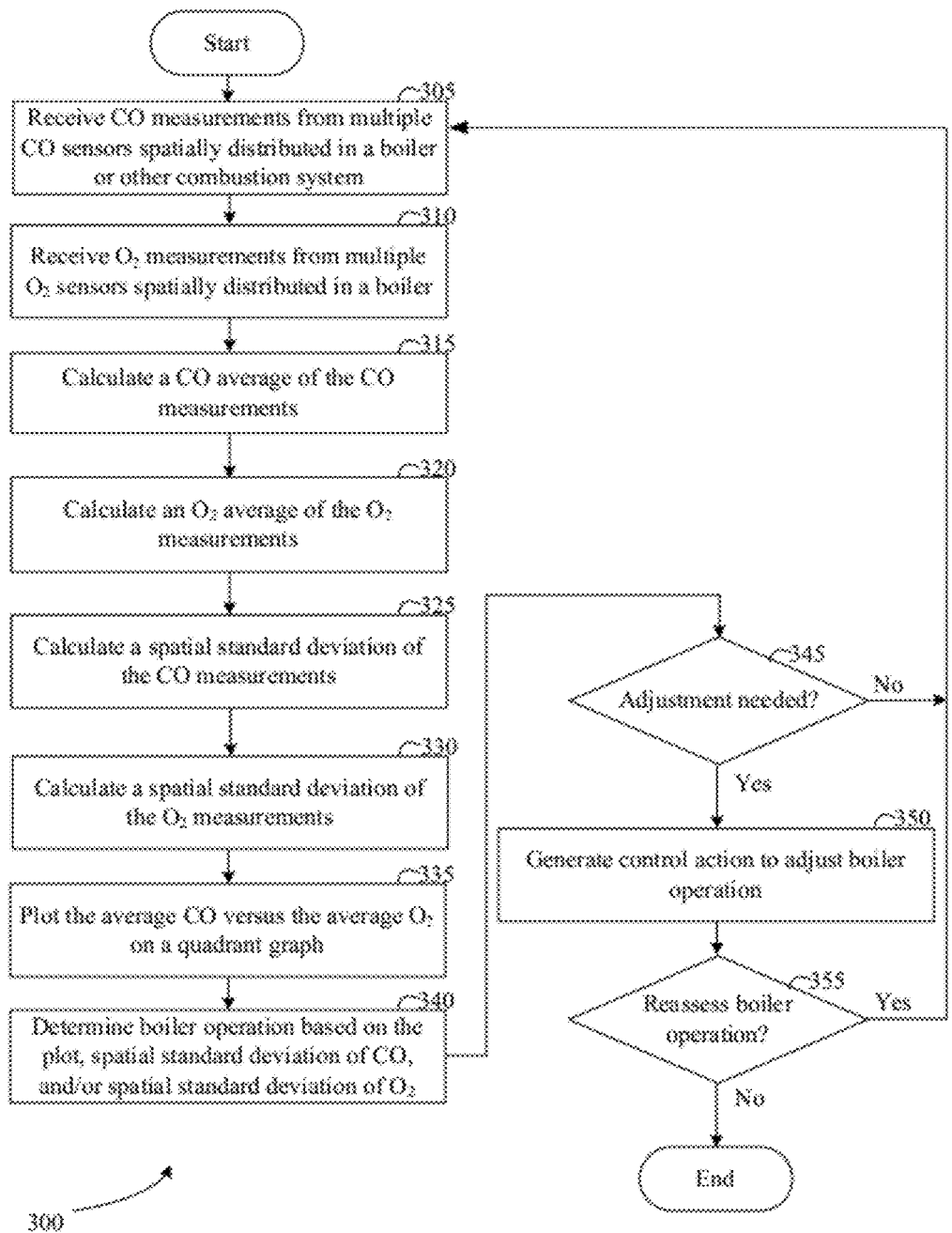
FIG. 3 is a flowchart illustrating a method for analyzing combustion system operation according to an example embodiment.

FIG. 3 illustrates an example method 300 for analyzing boiler performance and, if called for, adjusting boiler operation based on the current boiler operating conditions. Some or all of the operations of the method 300 may be performed, at least in part, by operating logic implemented by one or more controllers, such as described with reference to FIG. 9. The method 300 may begin at blocks 305 and 310, in which multiple CO measurements and multiple $O_2$ measurements are received from multiple CO sensors and $O_2$ sensors spatially distributed throughout the boiler. For example, the CO sensors 208 and the $O_2$ sensors 209 described with reference to FIG. 2 may be in communication with the controller and transmit to the controller sensed CO measurements and $O_2$ measurements. Capturing CO measurements and $O_2$ measurements corresponding to conditions at multiple locations through the boiler allows analyzing the operating condition of the boiler based on specific conditions at multiple individual locations within the boiler.

Figure 6:
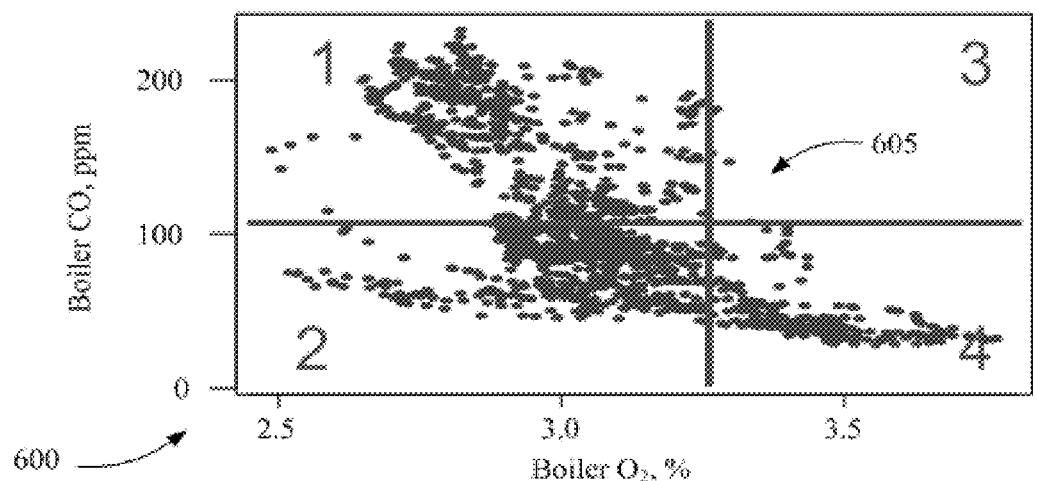
FIGS. 6-8 are representations of example combustion system analyses outputs, according to example embodiments.

According to one embodiment, the measurements captured at blocks 305 and 310 may be one measurement for each sensor at the same point in time, representing the CO and $O_2$ condition at each of the sensor locations at that point in time. According to another embodiment, the multiple measurements captured at blocks 305, 310 may include multiple measurements for each sensor taken over a period of time (e.g., seconds, minutes, etc.). Capturing multiple measurements over time (temporal measurements) allows representing the changing conditions at each of the sensors over time. The multiple measurements taken over time allow generating an average over time for each of the sensors, as well as performing a rolling temporal standard deviation calculation, such as may be useful to determine whether the boiler is in a steady state operating condition. FIG. 6 represents a graphic output of temporal measurements of a single sensor group (CO relative to $O_2$) over time, as described in more detail below. Determining steady state boiler conditions is also described in more detail with reference to FIG. 4.

Figure 7:
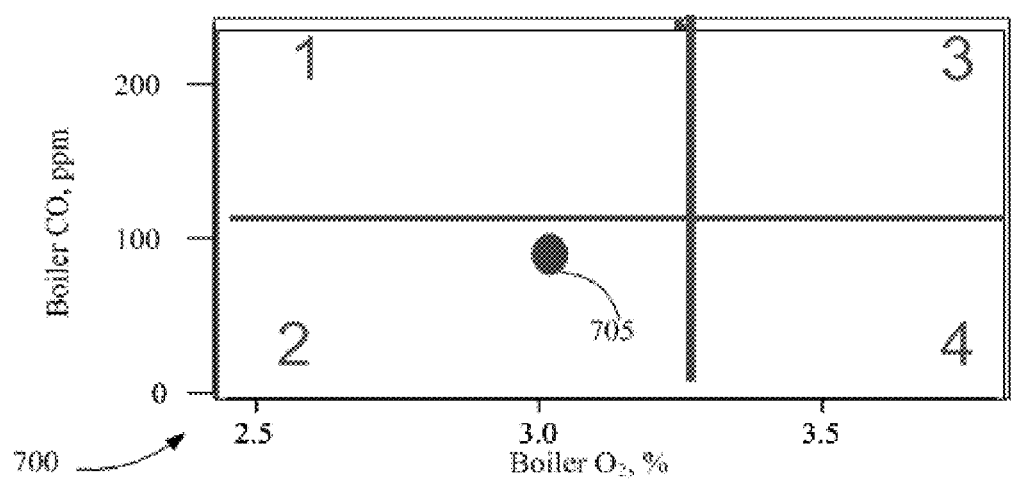
Figure 8:
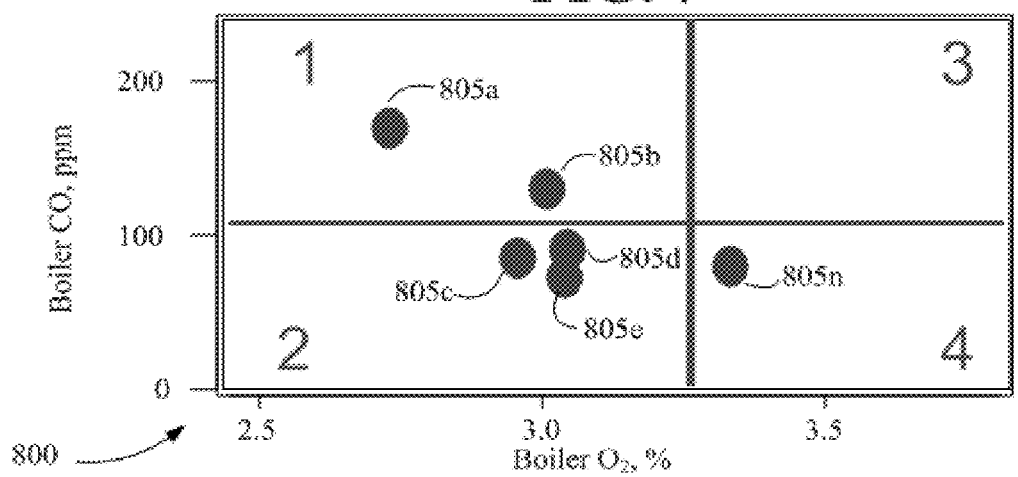

Following blocks 305 and 310 are blocks 315 and 320, in which an average of at least a subset of the multiple CO and $O_2$ measurements is calculated, respectively, according to one embodiment. The average may be an average across all spatially distributed sensors, such that the average represents overall boiler CO and $O_2$ conditions. In another embodiment, the average may be an average of temporal measurements for each respective sensor, such that each average represents an average CO and $O_2$ condition for each sensor area over the given time. FIG. 7 represents a graphic output of an average of temporal measurements taken from a single sensor (or a single co-located group of sensors) taken over time. FIG. 8 represents a graphic output of multiple averages, each representing an average of temporal measurements from a single sensor or sensor group taken over time.

Following blocks 315 and 320 are blocks 325 and 330 in which a spatial standard deviation is calculated for the multiple spatially distributed CO measurements and the multiple spatially distributed CO and $O_2$ measurements, respectively, according to one embodiment. Spatial standard deviation generally refers to the standard deviation of multiple spatially distinct measurements, such as each measurement taken from multiple spatially distributed sensors within the boiler. Thus, the spatial standard deviation generally measures the degree of variance between the conditions measured at the multiple spatially distributed sensors.

After calculating the spatial standard deviation for the CO and $O_2$ measurements, block 335 follows, in which the CO average versus the $O_2$ average is plotted graphically. Any number of graphical representations may be utilized to plot the average, including, but not limited to, x-y scatter plots, line graphs, and the like. According to one embodiment, a quadrant graph composed of four individual quadrants defined by the $O_2$ value along one axis (e.g., the x axis) and the CO value along the other axis (e.g., the y axis) may be provided with the plot representing the intersection of the CO average and the $O_2$ average in an x-y scatter plot fashion. FIGS. 6-8 illustrate example quadrant graphs, with FIGS. 7 and 8 illustrating a quadrant graph of a CO average versus the $O_2$ average. Moreover, according to other embodiments, values may not be plotted graphically, but may simply be maintained in data and subsequent analyses performed on the stored data values in a similar manner as would be done utilizing the relative location of the plot or plots on a quadrant graph compared to predefined threshold values that would otherwise define the graph quadrants.

Following block 335 is block 340, in which the boiler operating condition is inferred, depending at least in part on one or more of: the relative level of CO, the relative level of $O_2$, and/or the spatial standard deviation of CO and $O_2$. For example, according to one embodiment, thresholds may be defined to indicate high and/or low levels of CO and $O_2$, as well as, optionally, high and/or low spatial standard deviations of each of CO and $O_2$. Thus, in an embodiment in which the relative levels of CO and $O_2$ averages are plotted on a quadrant graph, the quadrants may be defined by these predefined thresholds of low and high CO and $O_2$ levels. In one embodiment, these thresholds, and thus the quadrant representations, may be adjustable and, thus, customizable for certain conditions or boiler operating states. This boiler analysis can, therefore, be performed having one set of predefined thresholds, and separately performed with different predefined thresholds to accommodate different goals and/or boiler operations. An example of an analysis performed at block 340 is described in more detail with reference to FIG. 5.

Figure 5:
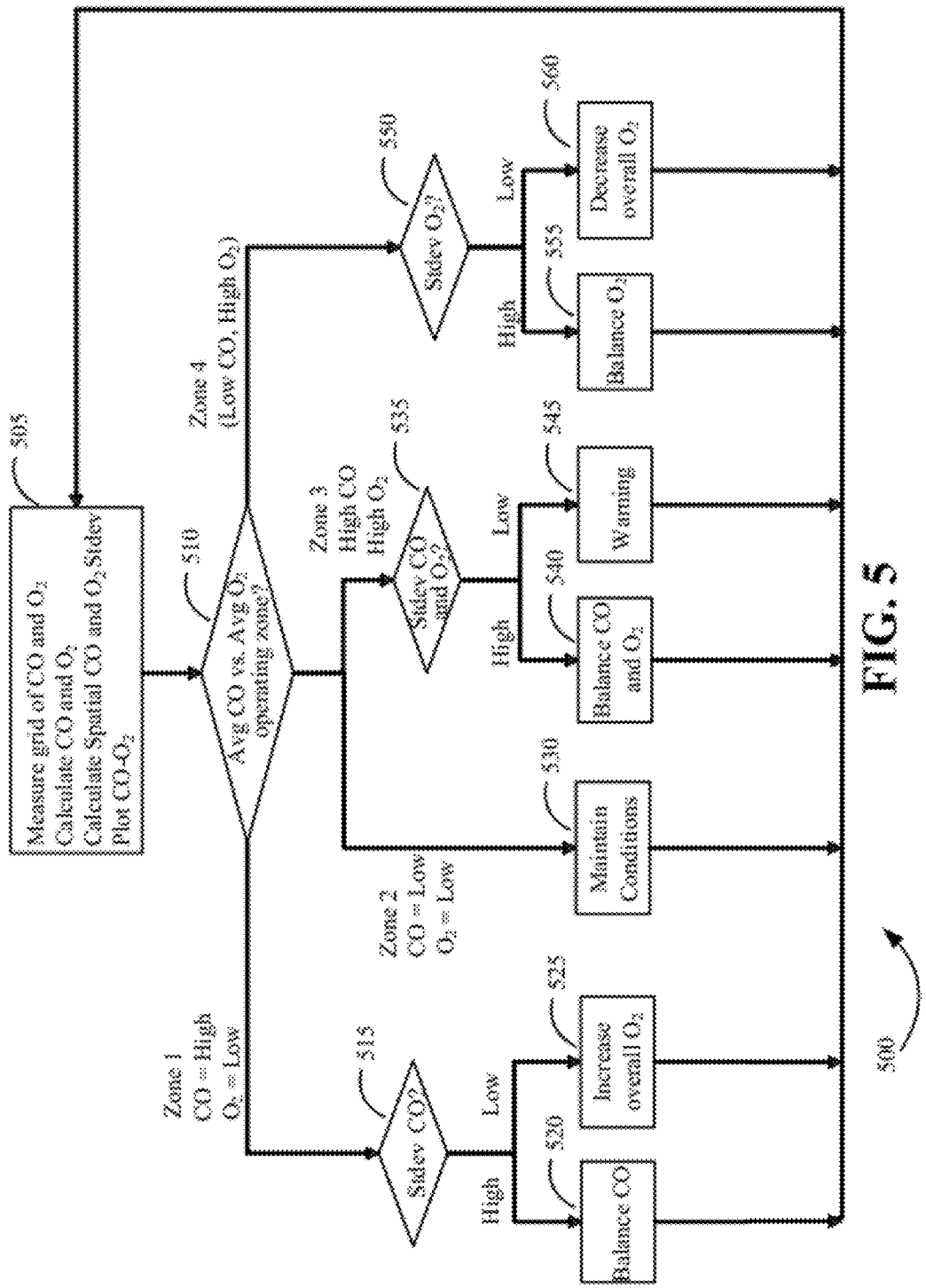
FIG. 5 is a flowchart illustrating a method for analyzing combustion system operation according to an example embodiment.

Now, with reference to FIG. 5, a flowchart representing a method 500 illustrating example processing logic for determining the boiler operating condition is provided, according to one embodiment. The method 500 may begin at block 505, in which the CO and $O_2$ measurements are taken, averages are calculated, spatial standard deviations are calculated, and the CO value(s) versus the $O_2$ value(s) are plotted on a quadrant graph, such as described with reference to blocks 305-335 of FIG. 3.

After plotting the CO value(s) versus the $O_2$ value(s) on a quadrant graph (or comparing according to any other number of techniques), the method 500 continues to decision block 510, in which it is determined which zone or quadrant the CO versus $O_2$ plot resides. Zones or quadrants may be defined according to the previously defined CO and $O_2$ value thresholds, such as are described with reference to block 340 of FIG. 3. For example, according to the embodiment illustrated in FIG. 5, zone 1 corresponds to high CO and low $O_2$ values, which would be the upper left quadrant if $O_2$ increases along the x-axis and CO increases along the y-axis; zone 2 corresponds to low CO and low $O_2$ values, which would be the lower left quadrant; zone 3 corresponds to high CO and high $O_2$ values, which would be the upper right quadrant; and zone 4 corresponds to low CO and high $O_2$ values, which would be the lower right quadrant. FIGS. 6-8 illustrate the relative positions of the four zones in quadrant graphs.

If it is determined at decision block 510 that the CO versus $O_2$ plot resides in zone 1 (high CO and low $O_2$), then blocks 515-525 follow. At decision block 515, it is determined if the spatial standard deviation of CO is high or low, such as relative to one or more predefined thresholds. If the spatial standard deviation of CO is high, then at least one control action may be generated at block 520 to attempt to balance the CO within the boiler. If the spatial standard deviation of CO is low, then at least one control action may be generated at block 525 to increase the overall $O_2$ within the boiler.

If it is determined at decision block 510 that the CO versus $O_2$ plot resides in zone 2 (low CO and low $O_2$), then it may be determined that the boiler is operating at a desirable operating condition at block 530 and no further control actions are necessary.

If it is determined at decision block 510 that the CO versus $O_2$ plot resides in zone 3 (high CO and high $O_2$), then blocks 535-545 follow. At decision block 535, it is determined if the spatial standard deviation of CO and the spatial standard deviation of $O_2$ is high or low. If the spatial standard deviation values of both are high, then at least one control action may be generated at block 540 to attempt to balance both CO and $O_2$ within the boiler. If the spatial standard deviation values of both are low, then at least one control action may be generated at block 545 to indicate the boiler is operating at an undesirable operating condition. Example control actions performed at block 545 may be, but are not limited to, generating a warning, sounding an alarm, writing data to memory, generating a report, halting boiler operations, halting other plant system operations, or any other similar action that may be desired when the boiler is operating at an undesirable operating condition.

If it is determined at decision block 510 that the CO versus $O_2$ plot resides in zone 4 (low CO and high $O_2$), then blocks 550-560 follow. At decision block 550, it is determined if the spatial standard deviation of $O_2$ is high or low, such as relative to one or more predefined $O_2$ thresholds. If the spatial standard deviation of $O_2$ is high, then at least one control action may be generated at block 555 to attempt to balance the $O_2$ within the boiler. If the spatial standard deviation of $O_2$ is low, then at least one control action may be generated at block 560 to decrease the overall $O_2$ within the boiler.

The processing logic illustrated by the method 500 of FIG. 5 may allow for repeating the operations, such that the method 500 repeats to block 505 to capture new CO and $O_2$ values and perform the same or similar analyses based on these new values.

With continued reference to FIG. 3, block 340 is followed by decision block 345, in which it is determined whether an adjustment is needed, such as by utilizing a similar method to that just described with reference to FIG. 5. If no adjustments are needed, operations may return to block 305 to allow iteratively performing the method 300 for updated boiler operations. If adjustment is needed, block 350 follows in which at least one control action is generated to cause boiler adjustment. The control action may be any of a number of control actions including, but not limited to, adjusting CO levels, adjusting $O_2$ levels, firing efficiency, sounding an alarm, saving boiler operating condition data to memory, halting boiler operation, identifying boiler condition to an operator, and the like.

After block 350 is block 355, in which it is determined if additional boiler assessments are to be made. If so, operations repeat back to block 305, repeating the method 300 for the conditions at the now changed instant in time. By repeating the method 300, an iterative re-analysis of the current boiler operating condition can be made, such as after performing an adjustment by the control action generated at block 350. Moreover, repeating the method allows continually analyzing the boiler over time.

If no further analysis is to be performed, the method 300 may end after block 355, after having gathered CO and $O_2$ data, and mathematically analyzing and, optionally, graphically plotting the CO and $O_2$ values, to determine boiler operating condition and cause a change if desired.

Figure 4:
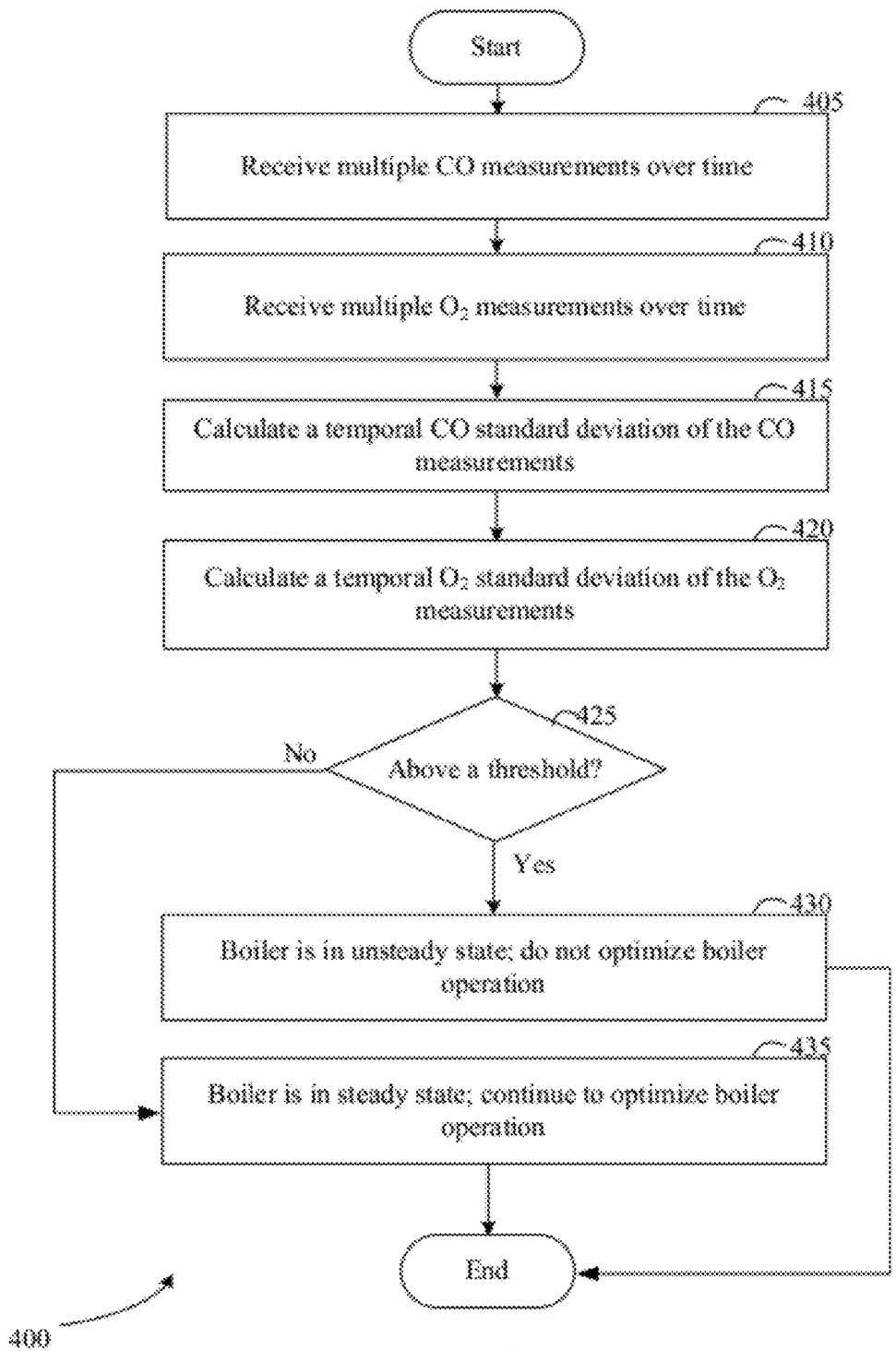
FIG. 4 is a flowchart illustrating a method for analyzing combustion system operation according to an example embodiment.

FIG. 4 illustrates another example method 400 for analyzing boiler performance, which includes analyzing a temporal standard deviation of CO measurements taken over time and a temporal standard deviation of $O_2$ taken over time. Aspects of the method 400 may be performed with the method 300 described with reference to FIG. 3, and/or the method 500 described with reference to FIG. 5, also allowing consideration of the temporal measurements when determining whether boiler adjustment should be performed, or whether the boiler is not in a steady state operation and not yet at a condition suitable for adjustment. The method 400 may begin at blocks 405 and 410, in which multiple CO measurements and multiple $O_2$ measurements taken over time are obtained, respectively. In one embodiment, these measurements are obtained from multiple spatially distributed CO sensors and multiple spatially distributed $O_2$ sensors, such as the CO sensors 208 and the $O_2$ sensors 209 described with reference to FIG. 2. The time over which the measurements are taken may differ, according to various embodiments. For example, these measurements may be over a number of seconds or over a number of minutes. According to one embodiment, the temporal measurements are taken over a period of ten minutes or longer.

At blocks 415 and 420, temporal standard deviations may be obtained for each sensor, respectively, such that the state of each sensor can be determined to be operating at a steady state or an unsteady state based on the respective temporal standard deviation values. Temporal standard deviation values can be indicative of how much the CO or $O_2$ levels vary over time. Variance of the CO or $O_2$ levels can be analyzed to indicate whether the boiler is operating in a steady state or in an unsteady state. In some circumstances, it may not be desirable to attempt to analyze and/or adjust the boiler operation until it is operating at a relative steady state.

Accordingly, following blocks 415 and 420 is decision block 425. At decision block 425, it is determined whether the temporal standard deviation values for CO, $O_2$, or both are above a predefined threshold. Much like the thresholds defined for the raw or average CO and $O_2$ values, thresholds can be defined for the temporal CO and $O_2$ standard deviation values. It is appreciated that, according to various embodiments, the threshold values may differ for temporal CO standard deviation values and temporal $O_2$ standard deviation values. Moreover, in some embodiments, it may be that different sensors have different standard deviation thresholds associated therewith to accommodate anticipated greater variance in some areas of the boiler relative to other areas. In some embodiments, a high temporal standard deviation value associated with measurements taken from just a single CO or $O_2$ sensor may be enough to indicate unsteady state operation. However, in other embodiments, additional processing logic may be included to allow defining how many sensors have to have temporal standard deviation values that exceed the predefined threshold before unsteady state operation is indicated. For example, in one embodiment, unsteady state operation is indicated when a majority of one or both CO or $O_2$ sensors have temporal standard deviation values above a predefined threshold. In other embodiments, however, the processing logic may call for any other number of sensors to have temporal standard deviation values above the predefined thresholds, such as, but not limited to, more than one, at least two, twenty-five percent, seventy-five percent, etc. These values also may optionally differ between CO sensors and $O_2$ sensors.

Accordingly, at decision block 425, if it is determined that the temporal standard deviation value or values are above the predefined thresholds, then operations continue to block 430, in which it is determined that the boiler is not operating at steady state conditions, and, thus, further boiler analysis or adjustment should not be performed. If it is determined that the predefined thresholds are not exceeded (e.g., that more than a required amount of sensors are within the predefined thresholds), then operations continue to block 435. At block 435, further analysis and adjustment of the boiler can be performed, such as is described with reference to FIGS. 3 and 5.

Accordingly, the method 400 may end after block 435, having determined whether the boiler is operating in a steady or unsteady state based, at least in part, on temporal standard deviation values of CO and/or $O_2$ measurements taken over time from one or more sensors within the boiler.

FIGS. 6-8 are representations of example boiler analyses outputs, according to example embodiments. FIG. 6 represents a graphic output 600 of multiple temporal measurements 605 of a single sensor group (CO relative to $O_2$) plotted over time. The multiple measurements 605 of CO relative to $O_2$ taken over time may be useful in calculating a rolling average of the CO and $O_2$ levels at or near the sensor group location. In addition, the temporal measurements taken over time may be useful to determine temporal CO and $O_2$ standard deviation values, such as discussed with reference to FIG. 4.

FIG. 7 represents a graphic output 700 plotting an average 705 of temporal measurements taken from a single sensor (or a sensor group) taken over time, according to one embodiment. A similar graphic output may represent a plot of an average of multiple spatial measurements, each taken from a different one of multiple spatially distributed sensors taken at or near the same time.

FIG. 8 represents a graphic output 800 plotting multiple averages 805*a*-805*n*, each representing an average of multiple temporal measurements from a single sensor or sensor group taken over time, according to one embodiment.

Figure 9:
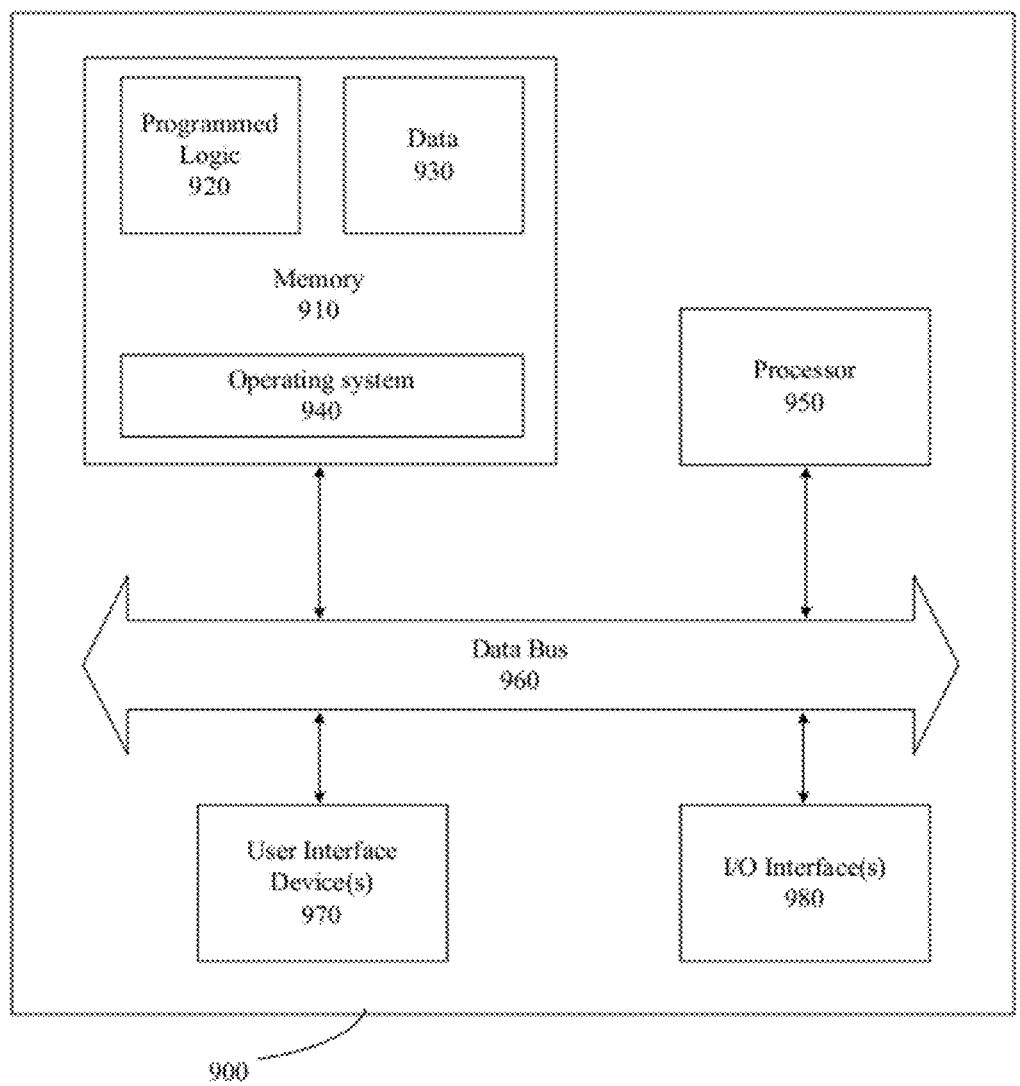
FIG. 9 is a block diagram illustrating a controller for modeling and/or controlling a turbine, according to an example embodiment.

FIG. 9 illustrates by way of a block diagram an example controller 900 used to analyze boiler operation, according to an illustrative embodiment. More specifically, the computerized controller 900 may be in communication with one or more of the CO and $O_2$ sensors, in addition to boiler control means. Thus, elements of the controller 900 may be used to generate, store, and operate predefined CO and $O_2$ threshold values for averages, individual measurements, and for temporal and/or spatial standard deviations, as well as the processing logic and display output described with reference to FIGS. 3-8, herein. The computerized controller 900 may include a memory 910 that stores programmed logic 920 (e.g., software) and may store data 930, such as sensed CO and $O_2$ measurements, threshold values, mathematical functions, and the like. The memory 910 also may include an operating system 940. A processor 950 may utilize the operating system 940 to execute the programmed logic 920, and in doing so, also may utilize the data 930. A data bus 960 may provide communication between the memory 910 and the processor 950. Users may interface with the controller 900 via at least one user interface device 970 such as a keyboard, mouse, control panel, or any other devices capable of communicating data to and from the controller 900. The controller 900 may be in communication with the boiler online while operating, as well as in communication with the boiler offline while not operating, via an I/O interface 980. More specifically, one or more of the controllers 900 may carry out the methods described with reference to FIGS. 3-5, including defining thresholds, analyzing CO and $O_2$ measurements, graphing and, optionally, displaying output, and generating control commands for use during boiler operation. Additionally, it should be appreciated that other external devices, multiple other boilers, and/or other components of the plant may be in communication with the controller 900 via the I/O interface 980. The controller 900 may be located remotely with respect to the boiler, according to one embodiment; although, in other embodiments, it may be co-located or even integrated with the boiler. Further the controller 900 and the programmed logic 920 implemented thereby may include software, hardware, firmware, or any combination thereof. It is also appreciated that multiple controllers 900 may be used, whereby different features described herein may be executed on one or more different controllers 900.

Accordingly, the embodiments described herein allow analyzing combustion system operations by comparing multiple CO measurements with multiple $O_2$ measurements taken from CO sensors and $O_2$ sensors distributed throughout the combustion system. These systems and methods can achieve the technical effect of identifying one or more operating conditions of a combustion system, such as a boiler, based at least in part on the levels of CO indicated by the CO measurements relative to the levels of $O_2$ indicated by the $O_2$ measurements, which can further consider the value differences at different locations within the boiler. Moreover, these systems and methods can achieve the technical effect of analyzing whether a combustion system, such as a boiler, is operating in a steady state or unsteady state, based on analyzing CO and/or $O_2$ measurements taken over time, which in turn allows adjusting the boiler operation only when operating at a relative steady state. Further technical effects achieved include adjusting combustion system operation based on the levels of CO relative to the levels of $O_2$ at one or more locations within the combustion system.

References are made to block diagrams of systems, methods, apparatuses, and computer program products according to example embodiments of the invention. It will be understood that at least some of the blocks of the block diagrams, and combinations of blocks in the block diagrams, respectively, may be implemented at least partially by computer program instructions. These computer program instructions may be loaded onto a general purpose computer, special purpose computer, special purpose hardware-based computer, or other programmable data processing apparatus to produce a machine, such that the instructions which execute on the computer or other programmable data processing apparatus create means for implementing the functionality of at least some of the blocks of the block diagrams, or combinations of blocks in the block diagrams discussed.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the block or blocks.

One or more components of the systems and one or more elements of the methods described herein may be implemented through an application program running on an operating system of a computer. They also may be practiced with other computer system configurations, including hand-held devices, multiprocessor systems, microprocessor based, or programmable consumer electronics, mini-computers, mainframe computers, etc.

Application programs that are components of the systems and methods described herein may include routines, programs, components, data structures, etc., that implement certain abstract data types and perform certain tasks or actions. In a distributed computing environment, the application program (in whole or in part) may be located in local memory, or in other storage. In addition, or in the alternative, the application program (in whole or in part) may be located in remote memory or in storage to allow for circumstances where tasks are performed by remote processing devices linked through a communications network.

Many modifications and other embodiments of the example descriptions set forth herein to which these descriptions pertain will come to mind having the benefit of the teachings presented in the foregoing descriptions and the associated drawings. Thus, it will be appreciated the invention may be embodied in many forms and should not be limited to the example embodiments described above. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A method for analyzing combustion system operation, comprising:
   receiving a first plurality of carbon monoxide (CO) measurements from a respective plurality of CO sensors distributed within a combustion system at a first point in time and a second plurality of CO measurements from the respective plurality of CO sensors at a second point in time;
   receiving a first plurality of oxygen ($O_2$) measurements from a respective plurality of $O_2$ sensors distributed within the combustion system at the first point in time and a second plurality of $O_2$ measurements from the respective plurality of $O_2$ sensors at the second point in time;
   calculating, for each of the respective plurality of CO sensors, a temporal standard deviation value of CO based on at least the first and second plurality of CO measurements;
   calculating, for each of the respective plurality of $O_2$ sensors, a temporal standard deviation value of $O_2$ based on at least the first and second plurality of $O_2$ measurements; and
   determining the operating state of the combustion system based on the temporal standard deviation calculations, wherein determining the operating state of the combustion system comprises:
      determining, for each of the respective plurality of CO sensors, if the temporal standard deviation value of CO meets or exceeds a predefined threshold associated with each of the respective plurality of CO sensors;
      determining, for each of the respective plurality of $O_2$ sensors, if the temporal standard deviation value of $0_$, meets or exceeds a predefined threshold associated with each of the respective plurality of $O_2$ sensors; and
      if a majority of the respective plurality of CO sensors have the temporal standard deviation value of CO above the predefined threshold associated with each of the respective plurality of CO sensors and if a majority of the respective plurality of $O_2$ sensors have the temporal standard deviation value of $O_2$ above the predefined threshold associated with each of the respective plurality of $O_2$ sensors, determining the combustion system is operating in an unsteady state.

2. A method for analyzing combustion system operation, comprising:
   receiving a first plurality of carbon monoxide (CO) measurements from a respective plurality of CO sensors distributed within a combustion system at a first point in time;

receiving a first plurality of oxygen ($O_2$) measurements from a respective plurality of $O_2$ sensors distributed within the combustion system at the first point in time;

determining at least one operating condition of the combustion system based at least in part on CO indicated by the first plurality of CO measurements relative to $O_2$ indicated by the first plurality of $O_2$ measurements;

receiving a second plurality of CO measurements from the same respective plurality of CO sensors at a second point in time;

receiving a second plurality of $O_2$ measurements from the same respective plurality of $O_2$ sensors at the second point in time;

calculating, for each of the respective plurality of CO sensors, a temporal standard deviation value of CO based on at least the first and second plurality of CO measurements;

calculating, for each of the respective plurality of $O_2$ sensors, a temporal standard deviation value of $O_2$ based on at least the first and second plurality of $O_2$ measurements; and making a second determination of at least one operating condition based at least in part on the temporal standard deviation calculations, wherein making the second determination of the at least one operating condition comprises:

determining, for each of the respective plurality of CO sensors, if the temporal standard deviation value of CO meets or exceeds a predefined threshold associated with each of the respective plurality of CO sensors;

determining, for each of the respective plurality of $O_2$ sensors, if the temporal standard deviation value of $O_2$, meets or exceeds a predefined threshold associated with each of the respective plurality of $O_2$ sensors; and if a majority of the respective plurality of CO sensors have the temporal standard deviation value of CO above the predefined threshold associated with each of the respective plurality of CO sensors and if a majority of the respective plurality of $O_2$ sensors have the temporal standard deviation value of $O_2$ above the predefined threshold associated with each of the respective plurality of $O_2$ sensors, determining the combustion system is operating in an unsteady state.

3. The method of claim 2, further comprising:
determining a CO average of the first plurality of CO measurements; and
determining an $O_2$ average of the first plurality of $O_2$ measurements;
wherein determining the at least one operating condition is further based at least in part on the CO average and the $O_2$ average.

4. The method of claim 3, further comprising:
plotting the CO average relative to the $O_2$ average in a quadrant graph of CO concentration versus $O_2$ concentration;
wherein determining the at least one operating condition is further based at least in part on a quadrant in which the plot of the CO average relative to the $O_2$ average is located.

5. The method of claim 4, wherein a vertical axis of the quadrant graph represents increasing CO concentration and a horizontal axis represents increasing $O_2$ concentration, wherein the quadrant graph comprises a lower left quadrant, an upper left quadrant, a lower right quadrant, and an upper right quadrant, each representing different operating conditions of the combustion system.

6. The method of claim 5, wherein determining the at least one operating condition further comprises:
if the plot of the CO average relative to the $O_2$ average is within a quadrant representing an acceptable operating condition, determining the combustion system is operating at an acceptable operating condition; and
if the plot of the CO average relative to the $O_2$ average is within a quadrant representing an undesirable operating condition, determining the combustion system is operating at an undesirable operating condition, and further comprising generating a control action to adjust at least one of the CO concentration or the $O_2$ concentration within the combustion system.

7. The method of claim 5, further comprising:
calculating a spatial standard deviation of CO based on the first plurality of CO measurements; and
calculating a spatial standard deviation of $O_2$ based on the first plurality of $O_2$ measurements.

8. The method of claim 7, wherein determining the at least one operating condition is based on at least one of: (a) the quadrant in which the plot of the CO average relative to the $O_2$ average is located; (b) the spatial standard deviation of CO; or (c) the spatial standard deviation of $O_2$.

9. The method of claim 7, wherein determining the at least one operating condition further comprises:
if the plot of the CO average relative to the $O_2$ average is located in the lower left quadrant, determining the combustion system is operating in an acceptable operating condition;
if the plot of the CO average relative to the $O_2$ average is located in the upper left quadrant and if the spatial standard deviation of CO meets or exceeds a predetermined threshold, determining the combustion system is operating in an unbalanced CO condition, and further comprising generating a control action to adjust the CO balancing in the combustion system;
if the plot of the CO average relative to the $O_2$ average is located in the upper left quadrant and if the spatial standard deviation of CO is below a predetermined threshold, determining the combustion system is operating in a low $O_2$ condition, and further comprising generating a control action to increase $O_2$ in the combustion system;
if the plot of the CO average relative to the $O_2$ average is located in the lower right quadrant and if the spatial standard deviation of $O_2$ meets or exceeds a predetermined threshold, determining the combustion system is operating in an unbalanced $O_2$ condition, and further comprising generating a control action to adjust the $O_2$ balancing in the combustion system;
if the plot of the CO average relative to the $O_2$ average is located in the lower right quadrant and if the spatial standard deviation of $O_2$ is below a predetermined threshold, determining the combustion system is operating in an increased $O_2$ condition, and further comprising generating a control action to decrease $O_2$ in the combustion system;
if the plot of the CO average relative to the $O_2$ average is located in the upper right quadrant and if the spatial standard deviation of CO or $O_2$ meets or exceeds a predetermined threshold, determining the combustion system is operating in an unbalanced CO or an unbalanced $O_2$ condition, and further comprising generating at least one control action to adjust at least one of CO balancing or $O_2$ balancing in the combustion system; and if the plot of the CO average relative to the O₂ average is located in the upper right quadrant and if the spatial standard deviation of CO and O₂ is below a predetermined threshold, determining the combustion system is operating in an undesirable condition, and further comprising generating at least one warning.

10. The method of claim 1, further comprising:
generating at least one control action to cause a change in the combustion system operation based at least in part on the at least one operating condition determined;
wherein making the second determination of at least one operating condition is further based at least in part on levels of CO indicated by the second plurality of CO measurements relative to levels of O₂ indicated by the second plurality of O₂ measurements.

11. The method of claim 1, wherein each of the first plurality of CO measurements represents an average of the first plurality of CO measurements taken over time from a respective one of the plurality of CO sensors, and wherein each of the first plurality of O₂ measurements represents an average of the first plurality of O₂ measurements taken over time from a respective one of the plurality of O₂ sensors.

12. A system for analyzing combustion system operation, comprising:
at least one controller in communication with a plurality of carbon monoxide (CO) sensors associated with a combustion system and a plurality of oxygen (O₂) sensors associated with the combustion system, wherein the at least one controller is configured to:
receive a first plurality of carbon monoxide CO measurements from a respective plurality of CO sensors distributed within a combustion system at a first point in time;
receive a first plurality of oxygen O₂ measurements from a respective plurality of O₂ sensors distributed within the combustion system at the first point in time;
determine at least one operating condition of the combustion system based at least in part on CO indicated by the first plurality of CO measurements relative to O₂ indicated by the first plurality of O₂ measurements;
receive a second plurality of CO measurements from the same respective plurality of CO sensors at a second point in time;
receive a second plurality of O₂ measurements from the same respective plurality of O₂ sensors at the second point in time;
calculate, for each of the respective plurality of CO sensors, a temporal standard deviation value of CO based on at least the first and second plurality of CO measurements;
calculate, for each of the respective plurality of O₂ sensors, a temporal standard deviation value of O₂ based on at least the first and second plurality of O₂ measurements; and
make a second determination of at least one operating condition based at least in part on a the temporal standard deviation calculations, wherein making the second determination of the at least one operating condition comprises:
determine, for each of the respective plurality of CO sensors, if the temporal standard deviation value of CO meets or exceeds a predefined threshold associated with each of the respective plurality of CO sensors;
determine, for each of the respective plurality of O₂ sensors, if the temporal standard deviation value of O₂ meets or exceeds a predefined threshold associated with each of the respective plurality of O₂ sensors; and if a majority of the respective plurality of CO sensors have the temporal standard deviation value of CO above the predefined threshold associated with each of the respective plurality of CO sensors and if a majority of the respective plurality of O₂ sensors have the temporal standard deviation value of O₂ above the predefined threshold associated with each of the respective plurality of O₂ sensors, determining the combustion system is operating in an unsteady state.

13. The system of claim 12, wherein the at least one controller is further configured to:
determine a CO average of the first plurality of CO measurements;
determine an O₂ average of the first plurality of O₂ measurements; and
determine the at least one operating condition based at least in part on the CO average and the O₂ average.

14. The system of claim 13, wherein the at least one controller is further configured to:
plot the CO average relative to the O₂ average in a quadrant graph of CO concentration versus O₂ concentration, wherein the vertical axis of the quadrant graph represents increasing CO concentration and the horizontal axis represents increasing O₂ concentration, wherein the quadrant graph comprises a lower left quadrant, an upper left quadrant, a lower right quadrant, and an upper right quadrant, each representing different operating conditions of the combustion system; and
determine the at least one operating condition based at least in part on the quadrant in which the plot of the CO average relative to the O₂ average is located.

15. The system of claim 14, wherein the at least one controller is further configured to determine the at least one operating condition by:
if the plot of the CO average relative to the O₂ average is within a quadrant representing an acceptable operating condition, determining the combustion system is operating at an acceptable operating condition; and
if the plot of the CO average relative to the O₂ average is within a quadrant representing an undesirable operating condition, determining the combustion system is operating at an undesirable operating condition; and
wherein, if the combustion system is operating at an undesirable operating condition, the at least one controller is further configured to generate a control action to adjust at least one of the CO concentration or the O₂ concentration within the combustion system.

16. The system of claim 14, wherein the at least one controller is further configured to:
calculate a spatial standard deviation of CO based on the first plurality of CO measurements; and
calculate a spatial standard deviation of O₂ based on the first plurality of O₂ measurements.

17. The system of claim 16, wherein the at least one controller is further configured to determine the at least one operating condition by:
if the plot of the CO average relative to the O₂ average is located in the lower left quadrant, determining the combustion system is operating in an acceptable operating condition;
if the plot of the CO average relative to the O₂ average is located in the upper left quadrant and if the spatial standard deviation of CO meets or exceeds a predetermined threshold, determining the combustion system is operating in an unbalanced CO condition, and wherein the at least one controller is further configured to generate a control action to adjust the CO balancing in the combustion system;

if the plot of the CO average relative to the $O_2$ average is located in the upper left quadrant and if the spatial standard deviation of CO is below a predetermined threshold, determining the combustion system is operating in a low $O_2$ condition, and wherein the at least one controller is further configured to generate a control action to increase $O_2$ in the combustion system;

if the plot of the CO average relative to the $O_2$ average is located in the lower right quadrant and if the spatial standard deviation of $O_2$ meets or exceeds a predetermined threshold, determining the combustion system is operating in an unbalanced $O_2$ condition, and wherein the at least one controller is further configured to generate a control action to adjust the $O_2$ balancing in the combustion system;

if the plot of the CO average relative to the $O_2$ average is located in the lower right quadrant and if the spatial standard deviation of $O_2$ is below a predetermined threshold, determining the combustion system is operating in an increased $O_2$ condition, and wherein the at least one controller is further configured to generate a control action to decrease $O_2$ in the combustion system;

if the plot of the CO average relative to the $O_2$ average is located in the upper right quadrant and if the spatial standard deviation of CO or $O_2$ meets or exceeds a predetermined threshold, determining the combustion system is operating in an unbalanced CO or an unbalanced $O_2$ condition, and wherein the at least one controller is further configured to generate at least one control action to adjust at least one of CO balancing or $O_2$ balancing in the combustion system; and if the plot of the CO average relative to the $O_2$ average is located in the upper right quadrant and if the spatial standard deviation of CO and $O_2$ is below a predetermined threshold, determining the combustion system is operating in an undesirable condition, and wherein the at least one controller is further configured to generate at least one warning.

18. The system of claim 12, wherein the at least one controller is further configured to:
generate at least one control action to cause a change in the combustion system operation based at least in part on the at least one operating condition determined;
and wherein the second determination of at least one operating condition is further based on levels of CO indicated by the second plurality of CO measurements relative to levels of $O_2$ indicated by the second plurality of $O_2$ measurements.

19. A method for analyzing combustion system operation, comprising:
receiving a first plurality of carbon monoxide (CO) measurements from a respective plurality of CO sensors distributed within a combustion system at a first point in time;
receiving a first plurality of oxygen ($O_2$) measurements from a respective plurality of $O_2$ sensors distributed within the combustion system at the first point in time;
determining at least one operating condition of the combustion system based at least in part on CO indicated by the first plurality of CO measurements relative to $O_2$ indicated by the first plurality of $O_2$ measurements;
receiving a second plurality of CO measurements from the same respective plurality of CO sensors at a second point in time;
receiving a second plurality of $O_2$ measurements from the same respective plurality of $O_2$ sensors at the second point in time;
making a second determination of at least one operating condition based at least in part on a temporal standard deviation calculation based on at least one of (a) the first and second plurality of CO measurements or (b) the first and second plurality of $O_2$ measurements;
determining a CO average of the first plurality of CO measurements;
determining an $O_2$ average of the first plurality of $O_2$ measurements, wherein determining the at least one operating condition is further based at least in part on the CO average and the $O_2$ average;
plotting the CO average relative to the $O_2$ average in a quadrant graph of CO concentration versus $O_2$ concentration, wherein determining the at least one operating condition is further based at least in part on a quadrant in which the plot of the CO average relative to the $O_2$ average is located wherein a vertical axis of the quadrant graph represents increasing CO concentration and a horizontal axis represents increasing $O_2$ concentration, and wherein the quadrant graph comprises a lower left quadrant, an upper left quadrant, a lower right quadrant, and an upper right quadrant, each representing different operating conditions of the combustion system;
calculating a spatial standard deviation of CO based on the first plurality of CO measurements; and
calculating a spatial standard deviation of $O_2$ based on the first plurality of $O_2$ measurements.

20. The method of claim 19, wherein determining the at least one operating condition is based on at least one of: (a) the quadrant in which the plot of the CO average relative to the $O_2$ average is located; (b) the spatial standard deviation of CO; or (c) the spatial standard deviation of $O_2$.

21. The method of claim 19, wherein determining the at least one operating condition further comprises:
if the plot of the CO average relative to the $O_2$ average is located in the lower left quadrant, determining the combustion system is operating in an acceptable operating condition;
if the plot of the CO average relative to the $O_2$ average is located in the upper left quadrant and if the spatial standard deviation of CO meets or exceeds a predetermined threshold, determining the combustion system is operating in an unbalanced CO condition, and further comprising generating a control action to adjust the CO balancing in the combustion system;
if the plot of the CO average relative to the $O_2$ average is located in the upper left quadrant and if the spatial standard deviation of CO is below a predetermined threshold, determining the combustion system is operating in a low $O_2$ condition, and further comprising generating a control action to increase $O_2$ in the combustion system;
if the plot of the CO average relative to the $O_2$ average is located in the lower right quadrant and if the spatial standard deviation of $O_2$ meets or exceeds a predetermined threshold, determining the combustion system is operating in an unbalanced $O_2$ condition, and further comprising generating a control action to adjust the $O_2$ balancing in the combustion system;
if the plot of the CO average relative to the $O_2$ average is located in the lower right quadrant and if the spatial standard deviation of $O_2$ is below a predetermined threshold, determining the combustion system is operating in an increased $O_2$ condition, and further comprising generating a control action to decrease $O_2$ in the combustion system;

if the plot of the CO average relative to the $O_2$ average is located in the upper right quadrant and if the spatial standard deviation of CO or $O_2$ meets or exceeds a predetermined threshold, determining the combustion system is operating in an unbalanced CO or an unbalanced $O_2$ condition, and further comprising generating at least one control action to adjust at least one of CO balancing or $O_2$ balancing in the combustion system; and if the plot of the CO average relative to the $O_2$ average is located in the upper right quadrant and if the spatial standard deviation of CO and $O_2$ is below a predetermined threshold, determining the combustion system is operating in an undesirable condition, and further comprising generating at least one warning.

\* \* \* \* \*